United States Patent
Murayama et al.

(10) Patent No.: US 6,423,085 B1
(45) Date of Patent: Jul. 23, 2002

(54) BIODEGRADABLE POLYMER COILS FOR INTRALUMINAL IMPLANTS

(75) Inventors: Yuichi Murayama; Fernando Vinuela, both of Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/406,306

(22) Filed: Sep. 27, 1999

Related U.S. Application Data

(63) Continuation of application No. PCT/US99/01790, filed on Jan. 27, 1999.
(60) Provisional application No. 60/072,653, filed on Jan. 27, 1998.

(51) Int. Cl.⁷ .............................................. A61M 29/00
(52) U.S. Cl. ...................... 606/200; 623/1.11; 623/1.38
(58) Field of Search .................. 606/200, 153, 606/154; 623/1.11, 1.38, 1.42, 1.45, 1.46, 1.48

(56) References Cited

U.S. PATENT DOCUMENTS

| | | | | |
|---|---|---|---|---|
| 4,994,069 A | * | 2/1991 | Ritchart et al. | 623/1.1 |
| 5,607,445 A | * | 3/1997 | Summers | 623/1.1 |
| 5,639,277 A | * | 6/1997 | Mariant et al. | 606/200 |
| 5,824,049 A | * | 10/1998 | Ragheb et al. | 623/1.1 |
| 5,837,008 A | * | 11/1998 | Berg et al. | 623/1.1 |

FOREIGN PATENT DOCUMENTS

| | | |
|---|---|---|
| JP | 10-127-647 | 5/1998 |
| JP | 11-47138 | 2/1999 |
| JP | 11-76249 | 3/1999 |

OTHER PUBLICATIONS

Robert C. Dawson III, George G. Shengelaia, Ali F. Krisht & Gary D. Bonner, Histologic Effects of Collagen–Filled Interlocking Detachable Coils in the Ablation of Experimental Aneyrysms in Swine, American Society of Neuroradiology, 17:853–858, May 1996.

Shinichi Tamatani, Tsunenori Ozawa, Takashi Minakawa, Shigekazu Takeuchi, Tetsuo Koike & Ryuichi Tanaka, Radiologic and Histopathologic Evaluation of Canine Artery Occlusion after Collegen–Coated Platinum Microcoil Delivery, American Journal of Radiology, 20:541–545, May 1996.
Robert C. Dawson, Ali F. Krisht, Daniel Borrow, Joseph Gregory, George G. Shengelaia, & Gary D. Bonner, Treatment of Experimental Aneurysms Using Collagen–coated Microcoils (Experimental Study), Neurosurgery 36: 133–140. 1995.

* cited by examiner

*Primary Examiner*—David O. Reip
*Assistant Examiner*—Julian W. Woo
(74) *Attorney, Agent, or Firm*—Daniel L. Dawes; Myers, Dawes & Andras LLP

(57) ABSTRACT

An endovascular cellular manipulation and inflammatory response are elicited from implantation in a vascular compartment or any intraluminal location of a separable coil comprised at least in part of at least one biocompatible and absorbable polymer or protein and growth factors. Typically a catheter associated with the separable coil is used to dispose the coil into a selected body lumen. The biocompatible and absorbable polymer or protein is thrombogenic. The coil further is comprised at least in part of a growth factor or more particularly a vascular endothelial growth factor, a basic fibroblast growth factor or other growth factors. The biocompatible and absorbable polymer is in the illustrated embodiment at least one polymer selected from the group consisting of polyglycolic acid, poly~glycolic acid poly-L-lactic acid copolymers, polycaprolactive, polyhydroxybutyrate/hydroxyvalerate copolymers, poly-L-lactide. Polydioxanone, polycarbonates, and polyanhydrides. The biocompatible and absorbable protein is at least one protein selected from the group consisting of collagen, fibrinogen, fibronectin, vitronectin, laminin, and gelatin. In one embodiment the coil is composed of the biocompatible and absorbable polymer or protein with a radio-opaque material is disposed thereon. Alternatively, the coil is composed of a radio-opaque material, and the biocompatible and absorbable polymer or protein is disposed thereon. This apparatus may be positioned within intracranial aneurysms or any aneurysm in the body as well as within other body cavities.

13 Claims, No Drawings

BIODEGRADABLE POLYMER COILS FOR INTRALUMINAL IMPLANTS

RELATED APPLICATIONS

The present application is related to U.S. Provisional Patent Application Ser. No. 60/072,653 filed Jan. 27, 1998 and is a continuation of PCT International Appl.No. PCT/US99/01790 filed Jan. 27, 1999 upon which its priority is based.

BACKGROUND OF THE INVENTION

1. Field of the Invention

The invention relates generally to the field of surgical and endovascular interventional instruments and specially to Intraluminal implants for occlusion of vessels or aneurysms.

2. Description of the Prior Art

Brain aneurysms are the commonest cause of nontraumatic subarachnoid hemorrhage (SAH) which is a significant life-threatening disease in adults. Annually in North America. the rupture of saccular aneurysms accounts for 25000 new cases of SAH. Microsurgical clipping of an aneurysm has been considered the gold standard for the treatment of this disease. Recently, intravascular treatment of aneurysms has become an accepted alternative technique. With the availability of microcatheters capable of accessing the intracranial circulation it has become possible to obliterate an aneurysm by filling it with soft platinum detachable coils (Guglielmi Detachable Coils; GDC). Use of the GDC system allows controlled delivery and detachment of platinum coils within an aneurysm.

Recent advances in endovascular techniques have proved valuable in the treatment of cerebral saccular aneurysms. GDCs have contributed especially to improvements in the endovascular management of cerebral aneurysms. However, the size of an aneurysm neck has an important effect on the anatomic results of aneurysm obliteration. It has been reported that in one study complete obliteration of aneurysms was achieved in 85% of small-necked aneurysms and 15% of wide-necked aneurysms.

Early experience with experimental and clinical use of Guglielmi detachable coils (GDCs) as manufactured by Target Therapeutics, Fremont, Calif., points to their effectiveness in the occlusion of endovascular small-necked intracranial saccular aneurysms.

However, the anatomical results of obliteration of either wide-necked (neck size ≧4 mm) or giant aneurysms using GDCs are generally unsatisfactory. The reasons for these incomplete anatomical results in wide-necked lesions include coil compaction, aneurysmal recanalization and the potential for distal migration of detached coils, i.e. the downstream loss of the coils from the aneurysm. Early intravascular re-endothelialization at the necks of aneurysms and the acceleration of wound healing in the aneurysmal sac and dome are potential solutions that may help achieve successful permanent cures of this type of aneurysm.

Some investigators have applied simple protein coatings on GDCs to enhance their thrombogenicity and wound healing properties. However, intravascular embolization techniques generally make use of small-diametered microcatheters for delivery of these coils. Simple protein coating, therefore, results in the problem of increasing the diameter of these coils which in turn causes them to stick within the lumen of a microcatheter during coil delivery.

Occlusion coils are used to occlude a site within a body lumen, such as a blood vessel, brain aneurysm, or vascular malformation. The coils are typically placed at a desired site within the lumen by means of a microcatheter. The coils are normally made of a radioopaque, biocompatible metals such as platinum, gold, or tungsten. In treating brain aneurysms the coils occlude the aneurysm by posing a physical barrier to blood flow and by promoting thrombus formation. The formation of the neo-endothelium and mature intra-aneurysmal thrombus is necessary prior to subsequent organization and scar formation that, in turn, yields a permanently occluded aneurysm.

In the presence of continued exposure of intra-aneurysmal coils to circulating blood, metallic coils can be insufficiently thrombogenic to promote the establishment of firm and mature thrombus within the aneurysm. They have difficulty in promoting endothelialization across the wide neck of an aneurysm. Therefore, it is advantageous to tightly pack the aneurysm with coils for complete cure of the aneurysms. This may cause a mass effect on adjacent the brain parenchyma or cranial nerves.

To accelerate wound healing in the aneurysm (i.e., promotion of scar formation) and to decrease the mass effect of the aneurysm, "biologically active" bioabsorbable embolic material may be useful. Bioabsorbable polymers, such as polyglycolic acid and polyglycolic/poly-L-lactic acid copolymers, or bioabsorbable proteins, such as collagen and gelatins, have been used to make Intraluminal implants. These bioabsorbable polymers or proteins are also used to provide a the drug delivery vehicle (such as for continuous local delivery of growth factors).

It is necessary to modify biological cellular response in preparation for acceleration of wound healing. Coil thrombogenicity was enhanced previously by increasing the surface area of the coils with fabric strands, such as Dacron, and by placing such coils into a thrombin solution. More recently, some investigators have modified the surfaces of platinum coils by coating them with collagen or polyurethane. This has resulted in some advantages, such as an increase in thrombogenicity of these coils. However, protein coatings on platinum surfaces are usually weak and may be removed easily during the delivery of the coils. Additionally, weakly coated proteins may be washed off by high-velocity arterial flow and may be a potential source of distal thromboemboli. There is also the potential problem of increases in the diameters of these coils; polyurethane coatings in particular also have the disadvantage of producing unfavorable changes in GDC performance, affecting their softness, thinness, smoothness, and memory shape.

In summary, GDCs and surrounding thrombus within an aneurysm are continuously exposed to and interact with circulating blood at the neck of the aneurysm. Coil compaction resulting from the force of pulsatile arterial blood flow is one of the reasons for incomplete obliteration of aneurysms. When this occurs, there is a potential risk of aneurysm recanalization and (re)rupture. Re-endothelialization and the promotion of wound healing in the aneurysmal sac and across its neck are necessary for complete aneurysm cure. Despite the many advantages of GDCs in the treatment of aneurysms, several recent clinical and experimental reports have highlighted their potential limitations in achieving an anatomic cure for wide-necked lesions. For example, two human autopsy cases treated with GDCs were reported for which the long-term (up to 6 months) histological findings revealed unorganized thrombus in the aneurysms, with no evidence of endothelialization across the aneurysmal neck in either case. Others have reported the histological findings for a patient with an anterior communicating artery aneurysm that had been previously treated with GDCs, in whom the compaction of coils resulted in an aneurysm remnant that was subsequently (6 months later) treated surgically. Histological examination of this resected aneurysm also revealed the presence of unorganized intra-aneurysmal thrombus that was exposed directly to the blood circulation without neointimal formation. It has been reported that in a long-term GDC study with experimental canine aneurysms, three of nine initially completely embolized aneurysms yielding to subsequent recanalization. Experimental GDC studies in monkey aneurysms were reported in which one of four of cases at 14 days of follow-up showed an aneurysmal "shoulder," indicative of aneurysm recanalization. More recently, in a study of experimental bifurcation aneurysms in rabbits, demonstrated the absence of organized thrombus and no neck endothelialization in treated aneurysms, even after follow-up periods of 3 to 6 months.

What is needed is a method to promote an inflammatory response and healing of the aneurysm with reduction of its mass effect.

BRIEF SUMMARY OF THE INVENTION

The invention is an intravascular device that modifies either accelerating or decreasing biological cellular response comprising a separable tip or coil comprised at least in part of at least one biocompatible and absorbable polymer or protein, and a placement device associated with the separable coil adapted to dispose the coil into a selected body lumen. The biocompatible and absorbable polymer or protein promotes an intra-aneurysmal inflammatory response and healing of the aneurysms. This device may carry growth factors, such as a vascular endothelial growth factor, a basic fibroblast growth factor or a mixture of several growth factors or cytokines. The separable tip, which also need not be a coil, need not be comprised of a polymer or protein, but may be comprised of any material now known or later devised which is biocompatible, absorbable and which promotes an intra-aneurysmal inflammatory response and promotes healing of the aneurysm.

The biocompatible and absorbable polymer is in the illustrated embodiment at least one polymer selected from the group consisting of polyglycolic acid, poly~glycolic acid/poly-L-lactic acid copolymers, polycaprolactive, polyhydroxybutyrate/hydroxyvalerate copolymers, poly-L-lactide, polydioxanone, polycarbonates, and polyanhydrides.

The biocompatible and absorbable protein is at least one protein selected from the group consisting of collagen, fibrinogen, fibronectin, vitronectin, laminin, and gelatin.

In one embodiment the coil is composed of the biocompatible and absorbable polymer or protein with a radioopaque material is disposed thereon. Alternatively, the coil is composed of a radio-opaque material, and the biocompatible and absorbable polymer or protein is disposed thereon.

The invention is also characterized as a method for forming a thrombus comprising the steps of providing a separable coil comprised at least in part of at least one biocompatible and absorbable polymer or protein and disposing the separable coil into a body lumen including the various combinations and examples described above.

The method further of comprises the step of providing the coil with a growth factor, and in particular a vascular endothelial growth factor (VEGF), a basic fibroblast growth factor (bFGF), or other growth factors.

The invention having been briefly summarized by the foregoing, the invention and its various embodiments may be better visualized by turning to the following drawings wherein like elements are referenced by like numerals.

DETAILED DESCRIPTION OF THE PREFERRED EMBODIMENTS

In the present invention a biodegradable polymer (or protein) coils are used to control thrombosis or accelerate wound healing of the brain aneurysms for which platinum coils sometimes have often proven unsatisfactory.

Another aspect of the invention is a method of drug delivery system using biodegradable polymer (or proteins) in the combination with growth factors such as vascular endothelial growth factor (VEGF), basic fibroblast growth factor (bFGF) or other growth factors which promote long lasting effect of the wound healing.

These biodegradable coils are useful for treating giant brain aneurysms to prevent the mass effect on the brain parenchyma or cranial nerves by shrinkage of scarring aneurysms.

Modes for Carrying Out the Invention

The implants of the invention may be placed within body lumens, e.g., blood vessels, Fallopian tubes, etc., of any mammalian species, including humans. The implant coils are made of biocompatible and absorbable polymers or proteins. Examples of bioabsorbable polymers that have been used in the illustrated embodiment to make Intraluminal implants include but are not limited to polyglycolic acid, poly~gycolic/poly-L-lactic acid copolymers, polycaprolactive, polyhydroxybutyrate/hydroxyvalerate copolymers, poly-L-lactide, polydioxanone, polycarbonates, and polyanhydrides. Examples of bioabsorbable proteins that have been used in the illustrated embodiment to make Intraluminal implants include but are not limited to collagen, fibrinogen, fibronectin, vitronectin, laminin and gelatin.

To achieve radioopacity, the bioabsorbable polymer coils may be coated or mixed with radioopaque materials such as tantalum or platinum. The bioabsorbable polymer or protein itself may be mounted or coated onto coils or wires of metals such as platinum or nitinol.

Preferred growth factors for use in the invention are the naturally occurring mammalian angiogenic growth such as VEGF, or b-FGF. Mixtures of such growth factors may also be used if desired.

The biodegradable polymer coils of the invention can be placed within the body lumen, vascular system or vessels using procedures well known in the art. Generally, the desired site within the vessel is accessed with a catheter. For small diameter torturous vessels the catheter may be guided to the site by the use of guide wires. Once the site has been reached, the catheter lumen is cleared by removing guide wire. In the case of polymer occlusion coils, the coils are loaded by means of a pusher wire. The coils may be attached to the distal end of the pusher via a cleavable joint (e.g., a joint that is severable by heat, electrolysis, electrodynamic activation or other means) or a mechanical joint that permits the coil to be detached from the distal end of the pusher wire by mechanical manipulation. Alternatively, the coils may be free and detached from the pusher wire, simply pushed through the catheter and expelled from the distal end of the catheter.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An endovascular apparatus of biodegradable and biocompatible polymers for developing a controlled inflammatory response with cellular manipulation in a selected aneurysm comprising:
    a separable coil comprised at least in part of at least one biocompatible and biodegradable polymer, which produces or enhances said inflammatory response with cellular manipulation to effect wound healing of said aneurysm, wherein said coil is adapted for disposition into said selected aneurysm; and
    an endovascular placement device associated with said separable coil.

2. The apparatus of claim 1 wherein said coil is composed of said biocompatible and biodegradable polymer, and wherein a radio-opaque material is disposed thereon.

3. The apparatus of claim 1 wherein said coil composed of a radio-opaque material, and wherein said biocompatible and biodegradable polymer is disposed thereon.

4. The apparatus of claim 1 wherein said biocompatible and biodegradable polymer promotes a controlled inflammatory response and controlled vascular healing.

5. The apparatus of claim 1 wherein said aneurysm is located within brain tissue and has a mass effect, and wherein said biocompatible and biodegradable polymer reduces said mass effect.

6. The apparatus of claim 1 wherein said biocompatible and biodegradable polymer comprises a synthetic biodegradable polymer or copolymer.

7. The apparatus of claim 6 wherein said synthetic biocompatible and biodegradable polymer is comprised of at least one synthetic polymer selected from the group consisting of polyglycolic acid, poly~glycolic acid/poly-L-lactic acid copolymers, polycaprolactive, polyhydroxybutyrate/hydroxyvalerate copolymers, poly-L-lactide, polydioxanone, polycarbonates, and polyanhydrides.

8. A method for producing an endovascular inflammatory response with cellular manipulation in an aneurysm comprising:
    providing a separable coil comprised at least in part of at least one biocompatible and biodegradable polymer, which bioactively produces or enhances said inflammatory response with cellular manipulation to effect wound healing of said aneurysm; and
    disposing said separable coil into said aneurysm.

9. The method of claim 8 wherein providing said separable coil comprised with said biocompatible and biodegradable polymer comprises providing said coil with at least one synthetic polymer selected from the group consisting of polyglycolic acid, poly~lycolic acid/poly-L-lactic acid copolymers, polycaprolactive, polyhydroxybutyrate/hydroxyvalerate copolymers, poly-L-lactide, polydioxanone, polycarbonates, and polyanhydrides.

10. The method of claim 8 wherein providing said coil provides a coil composed of said biocompatible and biodegradable polymer with a radio-opaque material is disposed thereon.

11. The method of claim 8 wherein providing said coil provides a coil composed of a radio-paque material with said biocompatible and biodegradable polymer is disposed thereon.

12. The method of claim 8 wherein said aneurysm is located within brain tissue and has a mass effect, and wherein providing a separable coil comprised at least in part of at least one biocompatible and biodegradable polymer or protein comprises reducing said mass effect.

13. The method of claim 8 wherein providing a separable coil comprised at least in part of at least one biocompatible and biodegradable polymer or protein comprises providing a synthetic biodegradable polymer or copolymer.

* * * * *

UNITED STATES PATENT AND TRADEMARK OFFICE
CERTIFICATE OF CORRECTION

PATENT NO.     : 6,423,085 B1                                    Page 1 of 1
APPLICATION NO. : 09/406306
DATED          : July 23, 2002
INVENTOR(S)    : Yuichi Murayama and Fernando Vinuela It is certified that error appears in the above-identified patent and that said Letters Patent is hereby corrected as shown below:

In the Specification

Col. 1, line 5, insert:

-- Government Rights
This invention was made with Government support under Grant No. NS042316 awarded by the National Institutes of Health. The Government has certain rights in this invention. --

Signed and Sealed this
Twenty-fifth Day of February, 2014

Michelle K. Lee
*Deputy Director of the United States Patent and Trademark Office*